(12) United States Patent
Simpson et al.

(10) Patent No.: US 6,258,750 B1
(45) Date of Patent: Jul. 10, 2001

(54) COMPLEXING COMPOSITIONS

(75) Inventors: Anthony Joseph Simpson, Cramlington; Stephen Wayne Heinzman; Barry Thomas Ingram, both of Whitley Bay, all of (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/601,293

(22) PCT Filed: Jan. 25, 1999

(86) PCT No.: PCT/IB99/00119

§ 371 Date: Jul. 31, 2000

§ 102(e) Date: Jul. 31, 2000

(87) PCT Pub. No.: WO99/38382

PCT Pub. Date: Aug. 5, 1999

(30) Foreign Application Priority Data

Jan. 31, 1998 (GB) .................................... 9802041

(51) Int. Cl.⁷ ............................ A01N 59/16; A01N 59/20
(52) U.S. Cl. ........................ 504/152; 504/187; 424/638; 424/641; 424/646
(58) Field of Search .................... 504/152, 187; 424/638, 641, 646

(56) References Cited

U.S. PATENT DOCUMENTS

| | | | |
|---|---|---|---|
| 3,158,635 | * 11/1964 | Kezerian et al. | 260/429 |
| 3,930,834 | * 1/1976 | Schulteis et al. | 71/67 |
| 5,741,555 | * 4/1998 | Wilson et al. | 427/437 |
| 6,069,113 | * 5/2000 | Kierzkowski et al. | 504/152 |

OTHER PUBLICATIONS

Abstracts #P002100086, Derwent Publications Ltd., London, GB, Jul. 7, 1993, Class C01, An 94–365177, Section ch, Week 9445.

Abstracts #84913 (XP00210084), Chemical Abstracts, vol. 117, No. 9, Aug. 31, 1992, Columbus, OH, Kovaleva, I.B. et al: "Dicarboxylic acis–biometal complexes as escologically safe stimulators for plant growth".

Abstracts #137517 (XP002100085), Chemical Abstracts, vol. 106, No. Apr. 27, 1987, Columbus, OH, Perov, N.N. et al.: "Testing iron, zinc, and manganese complexes with ethylenediaminediscuccinic and iminodisuccinic acids in chlorotic vineyards".

Abstracts #XP00210087, Derwent Publications Ltd., London, GB, Sep. 23, 1983, Class C04, An 84–145630, Section Ch, Week 8423.

Abstracts #XP002100088 & JP 0913687, Derwent Publications Ltd., London, GB, May. 27, 1987, Class C04, An 97–337018, Class C04, An 97–337018, section Ch, Week 9731.

* cited by examiner

Primary Examiner—S. Mark Clardy
(74) Attorney, Agent, or Firm—Kevin L. Waugh; Ian S. Robinson; Kim William Zerby

(57) ABSTRACT

The invention provides pesticidal, algicidal, herbicidal and/or fungicidal compositions, containing a complexing agent containing ethylene diamine disuccinic acid and one or selected metal ions, preferably cobalt, zinc or ions. The invention also relates to an aqueous pesticidal, algicidal, herbicidal, fungicidal composition comprising specific levels of calcium ions and complexing agent, containing a complex of a specific metal ion and a complexing a compound.

8 Claims, No Drawings

COMPLEXING COMPOSITIONS

TECHNICAL FIELD

The invention relates to pesticidal, algicidal, herbicidal and fungicidal compounds and compositions containing them. The invention also relates to the use of a specific complexing agent for preparation of a composition for inhibition or stabilisation of algae, plant and fungi growth.

BACKGROUND TO THE INVENTION

In almost all water systems such as rivers, lakes, streams, pools, industrial and ornamental water systems, irrigation systems etc., excessive growth of algae, (aquatic) plants and fungi can occur, which can be a severe problem, in particular because it can impart a distastefull appearance and odour to the water, it can interfere with the flow of the water, and may be harmfull to the growth or health of other life.

In the past, various types of algicides and herbicides have been employed in an attempt to control the growth of algae and aquatic plants. For example, dipyridylium compounds, as disclosed in U.S. Pat. No. 2,823,987 have been widely used to control the growth of algae and aquatic plants, and while these compounds have been effective, there are certain varieties of aquatic plants, such as Hydrilla, against which the dipyridylium compounds are relatively ineffective. Moreover, conventional herbicides have relatively little effect against algae.

Since the tun of the century, copper has been known as an effective control on algae, in particular copper sulfate. Not only is it probably one of the most effective chemical algicides it is also safe to use. Also cobalt is know to have algicidal properties. However, the solubility of copper salts such as sulfate salts, is severely affected by increasing alkaline pH's. In waters containing bicarbonates, carbonates and/or a pH over 7, it has long been known that copper sulfate is ineffective because of copper precipitating in the form of copper hydroxide or copper carbonate. Since the algicidal properties of copper sulfate are due to the copper ions, without these toxic copper ions, copper sulfate is essentially hainrmless to algae and the like.

Chelating agents, such as EDTA, have been used in combination with copper ions, to improve its solubility in alkaline environment, as for example described in U.S. Pat. No. 5,407,899 and EP 259,525. The chelating agent releases and maintains the toxic forms of copper, i.e. $Cu^{++}$, in the water.

However, the inventors have now found that not all chelating effectively release or maintain the level of dissolved copper ions. They have also found that a chelating agent does not perform effectively in all types of water system.

The inventors have now found that this can be due to the fact that these chelating agents may bind to other metal ions which may be present in the water. It has been found that in particular the presence of calcium ions can reduce the efficiency or effectiveness of certain chelating agents, such as EDTA. The nature of the systems and the methods wherein the chelating agents are used is such, that the presence of calcium ions is unavoidable or even desirable. Thus, this can lead to reduction of the chelating of the copper or cobalt ions, which subsequently can form insoluble salts and are thus no longer effective algicides.

This problem can be even more severe in several applications, where calcium-containing compounds are additionally required as algicides, for example calcium hypochlorite.

However, the inventors have now found that specific complexing agents are excellent complexing agents for forming complexes with the selected metal ions, useful in algicidal, herbicidal, fungicidal compositions, such as copper and cobalt ions, in particular in the presence of calcium ions.

SUMMARY OF THE INVENTION

The invention provides an aqueous pesticidal, algicidal, herbicidal and/or fungicidal composition, comprising calcium ions and one or more metal ions, selected from the group comprising Cu, Fe, Zn, Ni and Co (herein referred to as 'the selected metal ions'), and a complexing agent, whereby the $-\log_{10}C_T$ is equal to or greater than the smallest value of A or B, where $$A = -\log_{10}(L_T - M_T); \text{ and } B = K_1(1-K_2\sqrt{I})(1-K_3.\exp(-K_4.P)),$$

wherein $C_T$ is the total concentration of calcium ions, $L_T$ is the total concentration of incomplexing agent, $M_T$ is the total concentration of the metal ions, selected from the group consisting of Cu, Fe, Zn, Ni and Co; P is the pH of the composition, I is the ionic strength of the composition, wherein all concentrations are in moles/liter, where K1, K2, K3 and K4 are the following constants for the metals ions:

|    | $Cu^{++}$ | $Fe^{+++}$ | $Zn^{++}$ | $Ni^{++}$ | $Co^{++}$ |
|----|--------|---------|--------|--------|--------|
| K1 | 11.062 | 5.754   | 7.963  | 13.098 | 7.642  |
| K2 | 0.496  | 0.479   | 0.619  | 0.535  | 0.652  |
| K3 | 2.479  | 9385.0  | 24.202 | 1.473  | 32.069 |
| K4 | 0.227  | 1.092   | 0.506  | 0.126  | 0.532  |

Preferably, the selected metal ions are comprised in a complex with the complexing agent.

The invention also provides pesticidal, algicidal, herbicidal and/or fungicidal compositions, containing a complexing agent containing EDDS and one or more selected metal ions, preferably cobalt, zinc or copper ions.

The invention also relates to the use of a complexing agent and a selected metal ion, preferably a complex thereof, for preparation of pesticidal, algicidal, herbicidal and/or fungicidal compositions.

DETAILED DESCRIPTION OF THE INVENTION

Aqueous Compositions

In the aqueous composition of the invention, which are defined by a specific pH, the presence of a specific concentration of calcium ions, and the presence of one or more of the selected metal ions, and a specific level of complexing agents, preferably the selected metal ions and the complexing agent are present in the form of a complex.

The compositions can be used in any application where an algicidal, herbicidal or fungicidal is required, for example, the compositions of the invention may be used in pools, ponds or lakes and for protecting e.g. wood, roofs, walls, paths, paint, adhesives, glue, paper, textiles, leather, plastics, cardboard, lubricants, cosmetics, food, caulking, feed and industrial cooling water, but also crops such as rice.

The aqueous composition can be obtainable by a process comprising the step of addition of a complexing agent and one or more selected metal ions either separately or as a pre-mix composition in which they may be complexed, to an aqueous solution. The calcium ions may be added by incorporation in the pre-mix composition or may be present in the aqueous solution first to addition of complex and/or selected metal ion.

Alternatively, the aqueous composition can be obtainable by a process comprising the step of addition of a complexing agent to an aqueous solution comprising one or more of the selected metal ions, and calcium ions may be added by incorporation in the pre-mix composition or may be present in the aqueous solution first to addition of complex and/or selected metal ion.

Thus, it should be understood that in a preferred embodiment of the invention, the calcium ions may be present in the composition to be used, or may preferably be present in the composition when in use.

Preferred metal ions are zinc ions, cobalt ions and in particular copper ions. The complexing agent is preferably EDDS as described herein.

Preferably, a composition comprising both complexing agent and the selected metal ion in which the selected metal ion may be complexed with the complexing agent, is formed and subsequently added to the aqueous solution. To form such a complex, the complexing agent is generally used in a weight ratio of 0.20 to 5 parts to one part of the salt of the selected metal ion(s).

A copper-EDDS complex is a prefened complex for use in the compositions of the invention. Such a complex can be prepared by mixing an aqueous solution containing a salt of EDDS and an aqueous solution containing copper sulphate, preferably a copper sulphate complex, optionally combined with triethanolamine complex.

The proportions of the complexing agents and the selected metal ions can vary within wide limits, depending on the application of the compositions. Generally, the (complexes of the) complexing agent and the selected metal ions will be used at a level of 1% to 90% by weight of the compositions, whereby 30% to 70% are preferred.

The compositions of the invention can be applied directly to the subject or environment or solution which needs protection from the algae, plant and/or fungal growth or the elimination or reduction of the algae, plant and/or fungal growth, the compositions can be incorporated into another media, for example paints, coatings, agricultural sprays, and then applied to the subject or environment or solution which needs protection from the of algae, plant and/or fungal growth or the elimination or reduction of the algae, plant and/or fungal growth.

The composition can be applied in concentrated form or it can be diluted generally in the ratio of about 5 parts to 100 parts of water and the diluted solution is then applied, as described above.

Complexing Agents

A highly preferred complexing agents for use in aqueous compositions of the invention is N, N' ethylene diamine disuccinic acid or its salt ADDS).

It is known that the (S,S) EDDS isomer is more readily biodegradable than the (R,R) isomer. Thus, depending of the application of the aqueous compositions of the invention, it may be desirable to use only one of the isomers of EDDS. It may be preferred that a racemic mixture of the isomers is used in the aqueous compositions, for example because the racemic mixture is less expensive.

For the purpose of the invention and depending on the application of the aqueous composition, it should be understood that either the complexing agent can be introduced in the composition comprising the selected metal ions, to selectively form a complex with these metal ions, or the complexing agent can comprise one or more of the selected metal ions, prior to introduction into the composition (which can additionally contain one or more of the selected metal ions).

pH Measurement

The pH as used herein can be determined by any known method of calculating or measuring the pH of an aqueous solution.

Ionic Strength Measurement

The ionic strength (I) can be determined by the following equation:

$$I = \tfrac{1}{2}\Sigma c_i z_i^2,$$

wherein c is the molecular concentration of the soluble ion (i) and z is the charge of the soluble ion (i).

Additional Ingredients

The compositions of the invention can comprise any additional ingredients known in the art, which can be employed in algicidal, herbicidal or fungicidal compositions.

A preferred additional ingredient can be a source of chlorine, in particular calcium chloride. It can be preferred that the ratio of the complexing agent and the metal ion, preferably copper, to the source of chlorine be within the range 1:1 to 50:1.

Another preferred additional ingredient can be benzoic acid or salt or derivatives thereof.

Preferred additional ingredients can also be a buffer solution in water/alcohol or alcohol esters, for example: NaCl, NH4Cl, Na2SO4 and cetyl/oleic alcohol mono-ester in water.

(Polymeric) quaternary ammonium salts can also be useful additional ingredients in the compositions of the invention. A preferred compound can be dimethylbenzylammonium chloride.

Other ingredients can be benzoyl acids or derivatives thereof, benzene or benzene derivatives, such as cilorobenzene, nitrilobenzene and benzene imidazol, and cyano-derivatives.

It can be preferred that additionally builders, dispersants and/or crystal growth inhibitors are present. Preferred additional ingredients for incorporation in the aqueous compositions of the invention can be builders or dispersants, which selectively can bind calcium and magnesium ions. Any builder or dispersant material known in the art can be used. Particularly usefull builders or dispersants can be momomeric, oligomeric and polycarboxylate-containing components, polymeric components, borate-containing components and phosphate-containing components and silicate and aluminosilicate-containing components.

Preferred crystal growth inhibitors which can be present, preferably in addition to additional builders or dispersants, are phosphate-containing compounds. Suitable examples of water-soluble phosphate builders are the alkali metal tripolyphosphates, sodium, potassium and ammonium pyrophosphate, sodium and potassium and ammonium pyrophosphate, sodium and potassium orthophosphate, sodium polymeta/phosphate in which the degree of polymerisation ranges from about 6 to 21, and salts of phytic acid.

Suitable polycarboxylates or polycarboxylic acids can succinic acid, malonic acid, (ethylenedioxy) diacetic acid, maleic acid, diglycolic acid, tartaric acid, tartronic acid and fumaric acid; citrates, aconitrates and citraconates as well as succinate derivatives such as the carboxymethyloxysuccinates described in British Patent No. 1,379,241, lactoxysuccinates described in British Patent No. 1,389,732, and aminosuccinates described in Netherlands Application 7205873, and the oxypolycarboxylate materials such as 2-oxa-11,3-propane tricarboxylates described in British Patent No. 1,387,447; oxydisuccinates disclosed in British Patent No.

1,261,829, 1,1,2,2-eintane tetracarboxylates, 1,1,3,3-propane tetracarboxylates and 1,1,2,3-propane tetracarboxylates; sulfosuccinate derivatives disclosed in British Patent Nos. 1,398,421 and 1,398,422 and in U.S. Pat. No. 3,936,448, and the sulfonated pyrolysed citrates described in British Patent No. 1,439,000;

Polymeric components include the water soluble organic homo- or co-polymeric polycarboxylic acids or their salts in which the polycarboxylic acid comprises at least two carboxyl radicals separated from each other by not more than two carbon atoms.

Polymers of the latter type are disclosed in GB-A-1,596,756. Examples of such salts are polyacrylates of MWt 1,000–5,000 and their copolymers with maleic anhydride, such copolymers having a molecular weight of from 2,000 to 100,000, especially 40,000 to 80,000.

The polyamino components are usefull herein including those derived from aspartic acid such as those disclosed in EP-A-305282, EP-A-305283 and EP-A-351629.

Terpolymers containing monomer units selected from maleic acid, acrylic acid, polyaspartic acid and vinyl alcohol, particularly those having an average molecular weight of from 5,000 to 10,000, are also suitable herein.

Other polymeric components suitable for incorporation in the compositions herein include cellulose derivatives such as methylcellulose, carboxymethylcellulose, hydroxypropylmethylcellulose and hydroxyethylcellulose.

Further useful polymeric components are the polyethylene glycols, particularly those of molecular weight 1,000–10,000, more particularly 2,000 to 8,000 and most preferably about Other optional ingredients are amorphous or crystalline, preferably layered, silicate or aluminisilicate materials or builders. Suitable aluminosilicate zeolites have the unit cell formula $Na_z[(AlO_2)_z(SiO_2)y] \cdot xH_2O$ wherein z and y are at least 6; the molar ratio of z to y is from 1.0 to 0.5 and x is at least 5, preferably from 7.5 to 276, more preferably from 10 to 264. The aluminosilicate material are in hydrated form and are preferably crystalline, containing from 10% to 28%, more preferably from 18% to 22% water in bound form.

What is claimed is:

1. An aqueous algaecidal, herbicidal and/or fungicidal contrasting composition, comprising:
    a) from 1% to 90% by weight of the composition, a metal ion selected from the group consisting of copper, iron, zinc, nickel, cobalt ions and mixtures thereof,
    b) from 1% to 90% by weight of the composition, a complexing agent comprising ethylene diamine disuccinic acid or salt thereof; and
    c) a source of calcium and chlorine ions;

whereby the $-\log_{10}C_T$ is equal to or greater than the smallest value of A or B, and wherein $A=-\log_{10}(L_T-M_T)$; and $B=K_1[1-K_2(I)^{1/2}][1-K_3.\exp(-K_4.P)]$, wherein $C_T$ is the total concentration of calcium ions, $L_T$ is the total concentration of complexing agent, $M_T$ is the total concentration of the metal ions, selected from the group consisting of Cu, Fe, Zn, Ni, and Co; P is the pH of the composition, I is the ionic strength of the composition, wherein all concentrations are in moles/liter, and $K_1$, $K_2$, $K_3$ and $K_4$ are the following constants for the metal ions:

|  | $Cu^{++}$ | $Fe^{+++}$ | $Zn^{++}$ | $Ni^{++}$ | $Co^{++}$ |
| --- | --- | --- | --- | --- | --- |
| $K_1$ | 11.062 | 5.754 | 7.963 | 13.098 | 7.642 |
| $K_2$ | 0.496 | 0.479 | 0.619 | 0.535 | 0.652 |
| $K_3$ | 2.479 | 9385.0 | 24.202 | 1.473 | 32.069 |
| $K_4$ | 0.227 | 1.092 | 0.506 | 0.126 | 0.532 |

2. A composition according to claim 1, wherein the metal ions comprise copper and/or cobalt ions.

3. A composition according to claim 1, obtainable by a process comprising the step of addition of a complexing composition, comprising said metal ions and a complexing agent, to an aqueous solution, comprising calcium ions.

4. A composition according to claim 1 wherein said selected metal ion comprises from 30% to 70% by weight of the composition.

5. A composition according to claim 1 wherein said complexing agent comprises from 30% to 70% by weight of the composition.

6. A composition according to claim 1 wherein said source of chlorine ions falls within a range of 1:1 to 50:1 of said complexing agent and said metal ion(s) to said source of chlorine ions.

7. A composition according to claim 1 wherein said composition comprises from 0.2 to 5 parts said complexing agent to one part of the salt of the selected said metal ion(s).

8. A composition according to claim 1 wherein said source of chlorine ions comprises calcium chloride.

* * * * *